US00RE45625E

(19) United States
(12) Reissued Patent
Damiano

(10) Patent Number: US RE45,625 E
(45) Date of Reissued Patent: Jul. 28, 2015

(54) READING ENHANCEMENT DEVICE FOR PREVENTING AND TREATING PRESBYOPIA OF THE EYE

(71) Applicant: Richard Damiano, Littleton, CO (US)

(72) Inventor: Richard Damiano, Littleton, CO (US)

(73) Assignee: READING ENHANCEMENT CO.

(21) Appl. No.: 14/266,677

(22) Filed: Apr. 30, 2014

Related U.S. Patent Documents

Reissue of:
(64) Patent No.: 8,167,938
Issued: May 1, 2012
Appl. No.: 12/799,643
Filed: Apr. 29, 2010

U.S. Applications:
(63) Continuation of application No. 11/267,485, filed on Nov. 5, 2005, now Pat. No. 7,736,389, which is a continuation-in-part of application No. 11/210,236, filed on Aug. 23, 2005, now abandoned.

(60) Provisional application No. 60/603,965, filed on Aug. 23, 2004.

(51) Int. Cl.
*A61F 2/14* (2006.01)
*A61B 17/04* (2006.01)
*A61F 9/00* (2006.01)

(52) U.S. Cl.
CPC . *A61F 2/145* (2013.01); *A61F 2/14* (2013.01); *A61F 2/147* (2013.01); *A61F 9/0017* (2013.01)

(58) Field of Classification Search
CPC ..... A61F 2/145; A61F 9/0017
USPC ..... 623/4.1; 606/232
See application file for complete search history.

(56) References Cited

U.S. PATENT DOCUMENTS 5,354,331 A 10/1994 Schachar
5,465,737 A 11/1995 Schachar (Continued)

FOREIGN PATENT DOCUMENTS

WO WO 01/17460 A1 3/2001

OTHER PUBLICATIONS

U.S. Appl. No. 60/819,995, filed Jul. 11, 2006.

*Primary Examiner* — Jeffrey R Jastrzab
(74) *Attorney, Agent, or Firm* — Ramon L. Pizarro; Edwin H. Crabtree

(57) ABSTRACT

A reading enhancement device for preventing and/or treating presbyopia of the eye. The enhancement device is sutured to an outer wall of the sclera for buckling and compressing a portion of the sclera and the ciliary body inwardly and perpendicular to the plane of the sclera and exerting a posterior compression force toward the vitreous humor in the rear of the eye. The enhancement device includes a compression body with a front of the body having semi-circular convex surface. The compression body made of a non-metallic, synthetic polymer. The convex surface is used for engaging, buckling and compressing both a portion of the sclera and the ciliary body of the eye. The compression body also includes an enlarged, rounded first and second end portions and an elongated center portion with the convex surface formed thereon. Also, the compression body includes a rear having an outwardly extending rib portion with a pair of grooves at opposite ends of the rib portion. The grooves and the enlarged, rounded first and second end portions are used to aid the eye surgeon in suturing and securing the enhancement device to the side of the eye.

16 Claims, 2 Drawing Sheets

(56) References Cited

U.S. PATENT DOCUMENTS

| | | | |
|---|---|---|---|
| 5,489,299 | A | 2/1996 | Schachar |
| 6,007,578 | A | 12/1999 | Schachar |
| 6,214,044 | B1 | 4/2001 | Silverstrini |
| 6,280,468 | B1 | 8/2001 | Schachar |
| 6,682,560 | B1 | 1/2004 | Baikoff |
| 6,712,847 | B2 | 3/2004 | Baikoff et al. |
| 7,416,560 | B1 | 8/2008 | Schachar |
| 2002/0002403 | A1 | 1/2002 | Zdenek et al. |
| 2004/0098126 | A1 | 5/2004 | Freeman et al. |
| 2006/0004386 | A1 | 1/2006 | Caro |
| 2008/0091266 | A1 | 4/2008 | Griffis, III et al. |

READING ENHANCEMENT DEVICE FOR PREVENTING AND TREATING PRESBYOPIA OF THE EYE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This *reissue application of U.S. Pat. No. 8,167,938 is currently involved in pending inter-partes reexamination number 95/002,083, and is a* continuation patent application *and* claims the benefit of a non-provisional patent application Ser. No. 11/267,485 filed on Nov. 5, 2005 now U.S. Pat. No. 7,736,389*, which is involved in pending inter-partes reexamination 95/002,082*. Application Ser. No. 11/267,485 claims the benefit of an earlier filed non-provisional utility application Ser. No. 11/210,236 filed on Aug. 23, 2005. Application Ser. No. 11/210,236 claims the benefit of an earlier filed provisional application Ser. No. 60/603,965, by the subject inventor and filed on Aug. 23, 2004.

BACKGROUND OF THE INVENTION (a) Field of the Invention

This invention relates to a reading enhancement device sutured to the sclera of the eye for preventing and/or treating presbyopia and more particularly, but not by way of limitation, to a reading enhancement device for suturing to the outer wall of the sclera for buckling and compressing a portion of the sclera and the ciliary body inwardly and perpendicular to the plane of the sclera.

Presbyopia is well known as a reduction or loss of nearsight, usually present in the fourth or fifth decade of a person's age. The subject enhancement device exerts a posterior compressive force or centripetal force directed toward the vitreous humor in the rear of the eye and behind the crystalline eye lens and eye lens bag. The compressive force is perpendicular to the plane of the sclera and provides for movement of the eye lens and eye lens bag forward along a line of vision for the correction of presbyopia.

(b) Discussion of Prior Art

Heretofore, a number of differing theories have been described as to the physiology of the contraction of the ciliary body or ciliary muscle and tension on the zonule connected to the eye lens for the forward movement of the lens for the correction of presbyopia. For example, in U.S. Pat. Nos. 5,354,331, 5,465,737, 5,489,299 and 6,007,578 to Schachar, a theory for correcting for presbyopia is disclosed wherein the zonule ligament is placed in tension for flattening the periphery of the eye lens and creating a convex projection of the center of the lens.

In U.S. Pat. No. 6,682,560 to Baikoff, an element for correcting presbyopia is described. The corrective element is implanted in a tunnel in the sclera and in line with the ciliary body of the eye. The element has a geometric design for exerting a centripetal force on the ciliary body at an angle perpendicular to the optical axis of the eye. While this type of corrective design can be used for treating phakic individuals, it will have no effect on treating pseudophakic individuals. Also in the patent to Baikoff, the corrective element includes a rear wall for providing a pressure force oriented toward the center and the rear of the eye. This feature ensures compression of the vitreous humor and induces pressure and movement of the lens forwardly. While, the corrective element of Baikoff is somewhat similar to the subject invention, the Baikoff patent doesn't disclose or teach the importance of a reading enhancement device sutured to the outer wall of the sclera for directing an inward posterior compressive force perpendicular to the plane of the outer wall of the sclera. This key feature allows for the posterior compressive force to be directed behind the crystalline eye lens and eye lens bag for forward movement of the eye lens. The forward movement of the eye lens correcting for nearsight and based on a theory advocated by Van Helmholtz.

None of the above mentioned prior art patents specifically disclose the unique features, structure and function of the subject reading enhancement device sutured to the outer wall of the sclera for preventing and/or treating presbyopia of the eye as disclosed herein.

SUMMARY OF THE INVENTION

In view of the foregoing, it is a primary objective of the subject invention to provide an eye surgeon with a procedure for preventing and/or treating presbyopa of the eye for both phakic and pseudophakic individuals.

Another object of the invention is to create posterior compressive forces perpendicular to a plane of the sclera and directed inwardly and readwardly behind the crystalline eye lens and eye lens bag for forward movement of the eye lens.

Still another object of the reading enhancement device is the device's compression body is sutured directly to the outer wall of the sclera, so that a surgical incision in the sclera isn't necessary. This non-invasive procedure reduces the risk of infection and the length and cost of surgery. Also, because of this type of non-invasive procedure, there is less post operative pain and/or swelling and recovery time is reduced.

Yet another object of the invention is the procedure doesn't create adverse eye effects such as capillary constriction, necrosis and macular edema. Also, the use of one or more of the reading enhancement devices is completely reversible with no long term adverse consequences.

Further, the present invention may be used for one or both eyes with one or more of the devices evenly spaced around the iris at the junction of the pars plana and the ora serrata. The enhancement devices may vary in size and thickness for correcting for varying amounts of functional loss. For example, a thicker device can be used to correct vision of a person with 3 diopters of loss and a thinner device can be used to correct the vision of a person with 1 diopter of loss.

The subject reading enhancement device includes a compression body with a front of the body having semi-circular convex surface. The convex surface is used for engaging, buckling and compressing both a portion of the sclera and the ciliary body of the eye. The compression body also includes an enlarged, rounded first and second end portions and an elongated center portion with the convex surface formed thereon. Further, the compression body includes a rear having an outwardly extending rib portion with a pair of grooves at opposite ends of the rib portion. The grooves and the enlarged, rounded first and second end portions are used to aid the eye surgeon in suturing and securing the enhancement device to the side of the eye.

These and other objects of the present invention will become apparent to those in the medical profession familiar with various devices, methods and procedures for correcting for presbyopia when reviewing the following detailed description, showing novel construction, combination, and elements as herein described, and more particularly defined by the claims, it being understood that changes in the embodiments to the herein disclosed invention are meant to be included as coming within the scope of the claims, except insofar as they may be precluded by the prior art.

BRIEF DESCRIPTION OF THE DRAWINGS

The accompanying drawings illustrate preferred embodiments in the present invention according to the best modes presently devised for the practical application of the principles thereof, and in which.

DETAILED DESCRIPTION OF THE PREFERRED EMBODIMENTS

Figure 1:
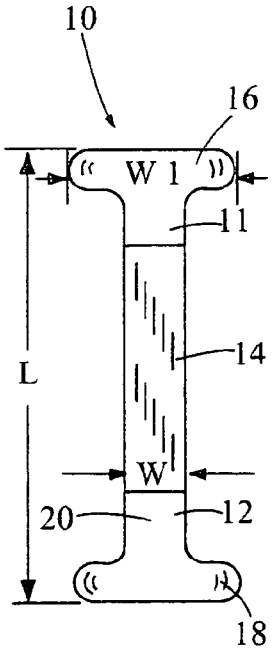
FIG. 1 is a front view of the subject reading enhancement device greatly enlarged and having an "I-beam" configuration. A front of the device includes a semi-circular convex surface used for engaging, buckling and compressing a portion of the sclera and ciliary body.
Figure 2:
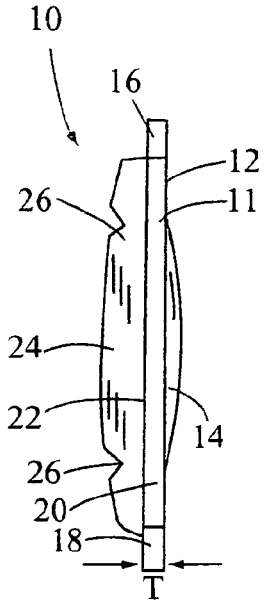
FIG. 2 is an enlarged side view of the enhancement device.

In FIG. 1, a front view of the enlarged subject reading enhancement device is shown having general reference numeral 10. The enhancement device 10 includes a compression body 11 with an "I-beam" configuration. A front 12 of the compression body 11 includes an outwardly extending semi-circular convex surface 14. A side profile of the convex surface 14 is shown in FIG. 2. The convex surface 14 is used for engaging, buckling and compressing both a portion of the sclera and the ciliary body of the eye. The compression body 11 also includes an enlarged, rounded first end portion 16, an enlarged, rounded second end portion 18 and an elongated center portion 20 with the convex surface 14 formed thereon.

The enhancement device 10 typically has a length "L" in a range of 3 to 6 mm, a width "W" of 0.5 to 2.0 mm, a width "W1" of 1.0 to 3.0 mm and a thickness "T", shown in FIG. 2, of the center portion 20 of 0.3 to 1.0 mm. Obviously, these dimension will vary depending on the eye application and method of engaging the side of the eye. Also, the device 10 can be made of either metallic or non-metallic materials, one or more different types of material, and treated with anti-infective or anti-inflammatory agents.

In FIG. 2, a side view of the enlarged enhancement device 10 is shown. In this drawing, the compression body 11 is shown with a rear 22 having an outwardly extending rib portion 24 having a pair of grooves 26 at opposite ends of the rib portion. The grooves 26 and the enlarged first and second end portions 16 and 18 are used to aid the surgeon in suturing and securing the enhancement device 10 to the side of the eye.

Figure 3:
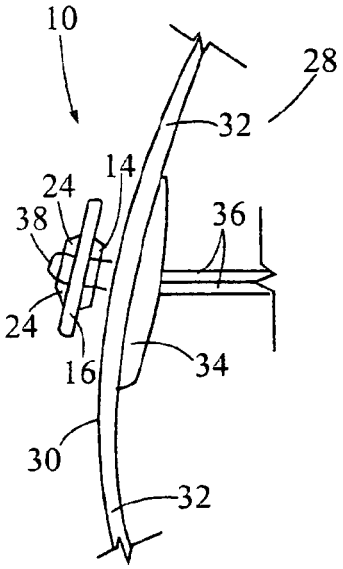
FIG. 3 is an enlarged end view of the enhancement device positioned next to a portion of the sclera and the ciliary body prior to suturing the device to the sclera.

In FIG. 3, an enlarged end view of the enhancement device 10 is shown positioned next to a side of an eye 28. The eye in the drawings is shown in cross section. In this view, the device 10 is disposed next to a portion of an outer wall 30 of a sclera 32 and a portion of the ciliary body 34. The ciliary body 34 is shown attached to one end of a zonule 36. In this drawing, the device 10 is illustrated with a portion of a suture 38 positioned for attaching it to the sclera 32.

Figure 4:
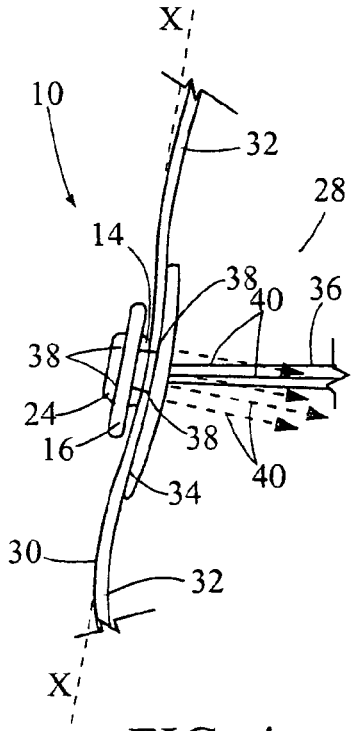
FIG. 4 is another enlarged end view of the enhancement device with the convex surface compressed against the sclera and the ciliary body and the device sutured thereto.

In FIG. 4, another enlarged end view of the enhancement device 10 is shown with the convex surface 14 compressed against a portion of the sclera 32 and the ciliary body 34. The compression body 11 is shown sutured to the sclera 32 using sutures 38. It should be noted that a key feature of the subject invention is the plane or length of the front 12 of the compression body 11 is disposed parallel to a planer surface of the sclera 32. The planer surface of the sclera 32 is shown along an axis X-X in this drawing.

When the device 10 has been properly sutured to the sclera 32 and along the length of the sclera, both the front 12 and the convex surface 14 compress or buckle inwardly the sclera 32 and the ciliary body 34. The attachment of the device 10 creates a compressive or centripetal force, shown as dashed lines 40, inwardly toward a vitreous humor 42 in the rear of the eye 28. It should be noted that the compressive force 40 is perpendicular to the axis X-X of the planer surface of the sclera 32. Also, by the nature of the sutures 38 attached to the sclera 32, added compressive forces 40 are directed inwardly toward the vitreous humor 38.

Figure 5:
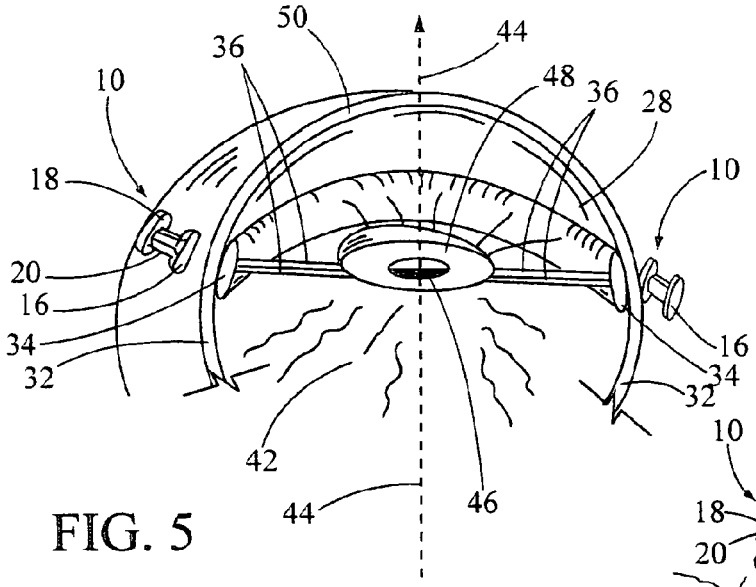
FIG. 5. is an enlarged perspective view and cross-section of an eye illustrating an crystalline eye lens and eye lens bag with a line of vision, shown as a dashed arrow, centered thereon. In this drawing, two of the enhancement devices are shown positioned for suturing to the sclera and on opposite sides of the eye.

In FIG. 5, an enlarged perspective view and cross-section of the eye 28 is shown and illustrating a line of vision, shown as a dashed line 44. The line of vision 44 is centered on a crystalline eye lens 46 inside an eye lens bag 48. In this drawing, two of the enhancement devices 10 are shown positioned for suturing to the sclera 32 on opposite sides of the eye 28. Also shown in the drawing is a cornea 50 of the eye 28. For proper balance of the compression forces 40 to the rear of the eye 28, two or more of the devices 10 will be equally spaced around the side of the eye 28 and sutured to the sclera 32, as shown in the drawings.

Figure 6:
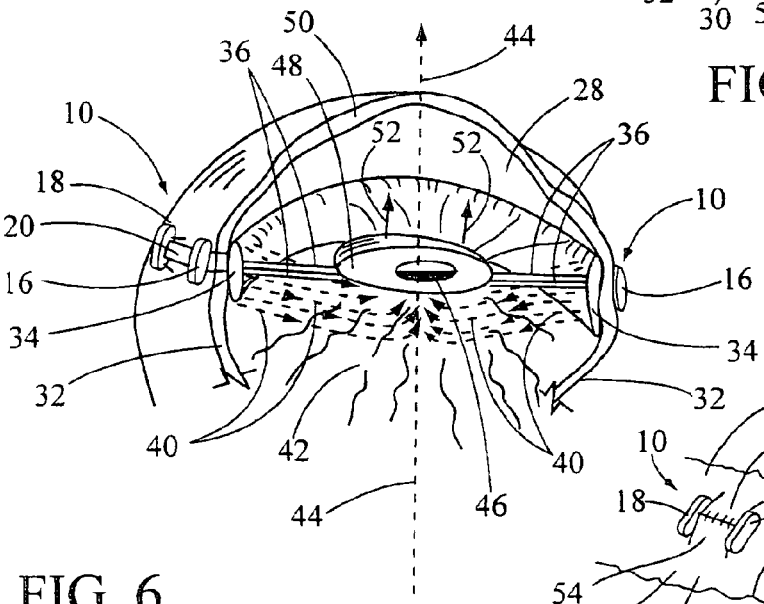
FIG. 6 is another enlarged perspective view and cross-section of the eye illustrating the two enhancement devices sutured to the sclera. The two devices are disposed parallel to the plane of the outer wall of the sclera. The devices compress and buckle the sclera and the ciliary body inwardly, thus creating a posterior compressive force, shown as dashed arrows, inwardly toward the vitreous humor in the rear of the eye and perpendicular to the plane of the sclera.

In FIG. 6, another enlarged perspective view and cross-section of the eye 28 is shown illustrating the two enhancement devices 10 sutured to a portion of the sclera 32. The devices 10 are disposed parallel to the plane of the sclera 32, as shown in FIG. 4, and compressed against the sclera 32 and the ciliary body 34 inwardly, thus creating posterior compressive forces 40, perpendicular to the plane of the sclera, directed inwardly toward the vitreous humor 42 in the rear of the eye 28. Because the compressive forces 36 are disposed behind the eye lens 46 and the eye lens bag 48, these forces in turn are directed upwardly, as shown in the drawing, and parallel to the line of vision 44. This key feature provides for pressure and forward movement, shown as arrows 52, of the eye lens 46 and the eye lens bag 48, thus helping prevent and/or treat presbyopia of the eye 28.

Figure 7:
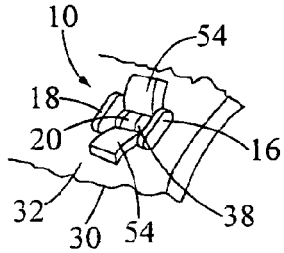
FIG. 7 is a perspective view of a portion of the sclera and illustrating an alternate way of securing the enhancement device to the sclera using a pair of sclera flaps cut in the outer wall of the sclera.

In FIG. 7, a perspective view of a portion of the sclera 32 is shown and illustrating an alternate way of securing the enhancement device 10 to the sclera 12. In this example, a pair of sclera flaps 54 are cut in the outer wall 30 of the sclera 32 forming an opening therein. The center portion 20 of one of the enhancement devices 10 is now placed next to the opening and sutured to the sclera 32 using sutures 38. While a pair of sclera flaps 32 are shown in this example, it can be appreciated that a single sclera flap 54 can be used equally well for securing the device 10 to the sclera and adding additional compressive force to the sclera and the ciliary body.

Figure 8:
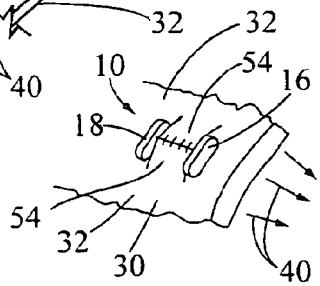
FIG. 8 is another perspective view of the portion of the sclera with the sclera flaps folded on top of a portion of the enhancement device and sutured together.

In FIG. 8, another perspective view of the portion of the sclera 32 is shown with the sclera flaps 54 folded on top of the center portion 20 of the device 10 and sutured together and tightened downwardly thereon. In this manner and using this procedure, added compressive pressure is applied to the enhancement device 10 for providing additional inward force in buckling and compressing the sclera and the ciliary body. Obviously, the use of the sclera flaps 54 is an alternate procedure when compared to securing the enhancement device 10 to the outer wall 30 of the sclera 32, as shown in FIGS. 4 and 6.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed except as precluded by the prior art.

The embodiments of the invention for which as exclusive privilege and property right is claimed are defined as follows:

1. A suture device for preventing and/or treating presbyopia of the eye, the suture device configured for suturing to the outer wall of the sclera to effect buckling and compressing a portion of the sclera, the suture device having a convex portion shaped to force the ciliary body inwardly thereby exerting a posterior compression force perpendicular to the sclera wherein the compression force strengthens the muscle of the ciliary body by reducing the stretching of the scleral spur occurring with age, the suture device comprising:

an I-beam shaped compression body having an elongated [semi-circular] convex center portion, the center portion of the I-beam shaped compression body terminating in transverse first and second ends, wherein the first end is adapted for receiving a first suture thereon and the second end is adapted for receiving a second suture thereon, wherein each of the first and second ends have a configuration preventing the first and second sutures from slipping off [the center portion] respectively; and the convex center portion having a tissue engaging surface extending outwardly from a front of the convex center portion and extending between the transverse first and second ends, the tissue engaging surface made of a compressible material, the compressible material reducing direct pressure on the blood vessels and nerves of the eye when engaging the outer wall of the sclera;

whereby when the transverse first end is sutured to the outer wall of the sclera using the first suture and the transverse second end is sutured to the outer wall of the sclera using the second suture, the tissue engaging surface of the [semi-circular] convex center portion is compressed against a portion of the outer wall of the sclera thereby exerting a compression force to the sclera.

2. The suture device as described in claim 1 wherein the compressible material of the tissue engaging surface is made of non-metallic, synthetic polymer.

3. The suture device as described in claim 1 wherein the compression body is treated with an anti-infective agent.

4. The suture device as described in claim 1 wherein the compression body is treated with an anti-inflammatory agent.

5. The suture device as described in claim 1 wherein the compression body includes a rib portion extending outwardly from a back of the center portion, opposite ends of the rib portion include a groove therein, the two grooves adapted for receiving the first and second sutures thereon.

6. The suture device as described in claim 1 wherein the compression body has a length "L" in a range of 3 to 6 mm, a width "W" in a range of 0.5 to 2.0 mm and a thickness "T" in a range of 0.3 to 1.0 mm.

7. A suture device for preventing and/or treating presbyopia of the eye, the suture device configured for suturing to the outer wall of the sclera to effect buckling and compressing a portion of the sclera, the suture device having a convex portion shaped to force the ciliary body inwardly thereby exerting a posterior compression force perpendicular to the sclera wherein the compression force strengthens the muscle of the ciliary body by reducing the stretching of the scleral spur occurring with age, the suture device comprising:

an I-beam shaped compression body having an elongated [semi-circular] convex center portion, the center portion of the I-beam shaped compression body terminating in transverse first and second ends, wherein the first end is adapted for receiving a first suture thereon and the second end is adapted for receiving a second suture thereon, wherein each of the first and second ends have a configuration preventing the first and second sutures from slipping off the center portion respectively;

the convex center portion having a tissue engaging surface extending outwardly from a front of the convex center portion and extending between the transverse first and second ends, the convex center portion made of a first material and the tissue engaging surface made of a second material, and a rib portion extending outwardly from a back of the convex center portion, opposite ends of the rib portion include a groove therein, the two grooves adapted for receiving the first and second sutures thereon;

whereby when the transverse first end is sutured to the outer wall of the sclera using the first suture and the transverse second end is sutured to the outer wall of the sclera using the second suture, the tissue engaging surface of the [semi-circular] convex center portion is compressed against a portion of the outer wall of the sclera thereby exerting a compression force to the sclera.

8. The suture device as described in claim 7 wherein the first and second materials are made of a non-metallic material.

9. The suture device as described in claim 7 wherein the first material is made of a hard, rigid material for maintaining the overall shape of the compression body and wherein the second material is made of a compressible material, the compressible material reducing direct pressure on the blood vessels and nerves of the eye when engaging the outer wall of the sclera.

10. The suture device as described in claim 7 wherein the compression body is treated with an anti-infective agent.

11. The suture device as described in claim 7 wherein the compression body is treated with an anti-inflammatory agent.

12. The suture device as described in claim 7 wherein the compression body has a length "L" in a range of 3 to 6 mm, a width "W" in a range of 0.5 to 2.0 mm and a thickness "T" in a range of 0.3 to 1.0 mm.

13. A suture device for preventing and/or treating presbyopia of the eye, the suture device configured for suturing to the outer wall of the sclera to effect buckling and compressing a portion of the sclera, the suture device having a convex portion shaped to force the ciliary body inwardly thereby exerting a posterior compression force perpendicular to the sclera wherein the compression force strengthens the muscle of the ciliary body by reducing the stretching of the scleral spur occurring with age, the suture device comprising:

an I-beam shaped compression body having an elongated [semi-circular] convex center portion, the center portion of the I-beam shaped compression body terminating in transverse first and second ends, wherein the first end is adapted for receiving a first suture thereon and the second end is adapted for receiving a second suture thereon, wherein each of the first and second ends have a configuration preventing the first and second sutures from slipping off the center portion respectively;

the convex center portion having a tissue engaging surface extending outwardly from a front of the convex center portion and extending between the transverse first and second ends, the convex center portion made of a first non-metallic material and the tissue engaging surface made of a second non-metallic material, the first material is made of a hard, rigid material for maintaining the overall shape of the compression body, the second material is made of a compressible material for reducing direct pressure on the blood vessels and nerves of the eye when engaging the outer wall of the sclera; and a rib portion extending outwardly from a back of the convex center portion, opposite ends of the rib portion include a groove therein, the two grooves adapted for receiving the first and second sutures thereon;

whereby when the transverse first end is sutured to the outer wall of the sclera using the first suture and the transverse second end is sutured to the outer wall of the sclera using the second suture, the tissue engaging surface of the convex center portion is compressed against a portion of the outer wall of the sclera thereby exerting a compression force to the sclera.

14. The suture device as described in claim 13 wherein the compression body is treated with an anti-infective agent.

15. The suture device as described in claim 13 wherein the compression body is treated with an anti-inflammatory agent.

16. The suture device as described in claim 13 wherein the compression body has a length "L" in a range of 3 to 6 mm, a width "W" in a range of 0.5 to 2.0 mm and a thickness "T" in a range of 0.3 to 1.0 mm.

* * * * *